US00PP34282P2

(12) United States Plant Patent
Lee

(10) Patent No.: US PP34,282 P2
(45) Date of Patent: May 31, 2022

(54) ***IMPATIENS* PLANT NAMED 'IMGZ0020'**

(50) Latin Name: *Impatiens interspecific*
Varietal Denomination: IMGZ0020

(71) Applicant: SYNGENTA CROP PROTECTION AG, Basel (CH)

(72) Inventor: Jaemin Lee, Gilroy, CA (US)

(73) Assignee: Syngenta Crop Protection AG, Basel (CH)

( * ) Notice: Subject to any disclaimer, the term of this patent is extended or adjusted under 35 U.S.C. 154(b) by 0 days.

(21) Appl. No.: 17/300,497

(22) Filed: Jul. 20, 2021

(51) Int. Cl.
*A01H 5/02* (2018.01)
*A01H 6/16* (2018.01)

(52) U.S. Cl.
USPC ..... Plt./317

(58) Field of Classification Search
USPC ..... Plt./317
See application file for complete search history.

*Primary Examiner* — Susan McCormick Ewoldt
(74) *Attorney, Agent, or Firm* — Dale Skalla

(57) ABSTRACT

A new *Impatiens* plant named 'IMGZ00020' particularly distinguished by the bright pink flower on medium peduncles on a medium sized well branched plant with dark green foliage.

1 Drawing Sheet

Latin name of the genus and species of the plant claimed: *Impatiens interspecific.*

Varietal denomination: 'IMGZ0020'.

BACKGROUND OF THE NEW PLANT

The present invention comprises a new *Impatiens*, botanically known as *Impatiens interspecific*, and hereinafter referred to by the variety name 'IMGZ0020'.

'IMGZ0020' is a product of a planned breeding program. The new cultivar has large, flat bright pink flowers. The foliage is dark green with light green veins on the upper and lower side of the leaf. The plant is medium sized and well branched.

'IMGZ0020' originated from a hybridization made in March 2017 in a controlled breeding environment in San Jose Pinula, Guatemala.

The female parent is designated as 'W5516-2' with white flower color. The male parent is designated as 'W0128-11' and is large sized and has rose color with pink marginal flower pattern.

The resultant seed was sown in November 2017 in a greenhouse in Gilroy, Calif. USA and 'IMGZ0020' was selected there as one flowering plant within the progeny of the stated cross in spring 2017.

The first act of asexual reproduction of 'IMGZ0020' was accomplished when vegetative cuttings were propagated from the initial selection in February 2018 in a controlled environment in Gilroy, Calif.

BRIEF SUMMARY OF INVENTION

Horticultural examination of plants grown from cuttings of the plant initiated in April 2018 in Gilroy, Calif. USA, has demonstrated that the combination of characteristics as herein disclosed for 'IMGZ0020' are firmly fixed and are retained through successive generations of asexual reproduction.

'IMGZ0020' has been observed under different environmental conditions. The phenotype may vary significantly with variations in environment such as temperature and light intensity.

A Plant Breeder's Right for this cultivar has not yet been applied for. 'IMGZ0020' has not been made publicly available prior to the effective filing date of this application, notwithstanding any disclosure that may have been made less than one year prior to the effective filing date of this application by the inventor or another who obtained 'IMGZ0020' directly from the inventor.

The following traits have been repeatedly observed and are determined to be basic characteristics of the new variety. The combination of these characteristics distinguishes this *Impatiens* as a new and distinct variety.

BRIEF DESCRIPTION OF THE PHOTOGRAPHS

The accompanying photographic drawings show typical flower and foliage characteristics of 'IMGZ0020' with colors being as true as possible with an illustration of this type.

Figure 1:
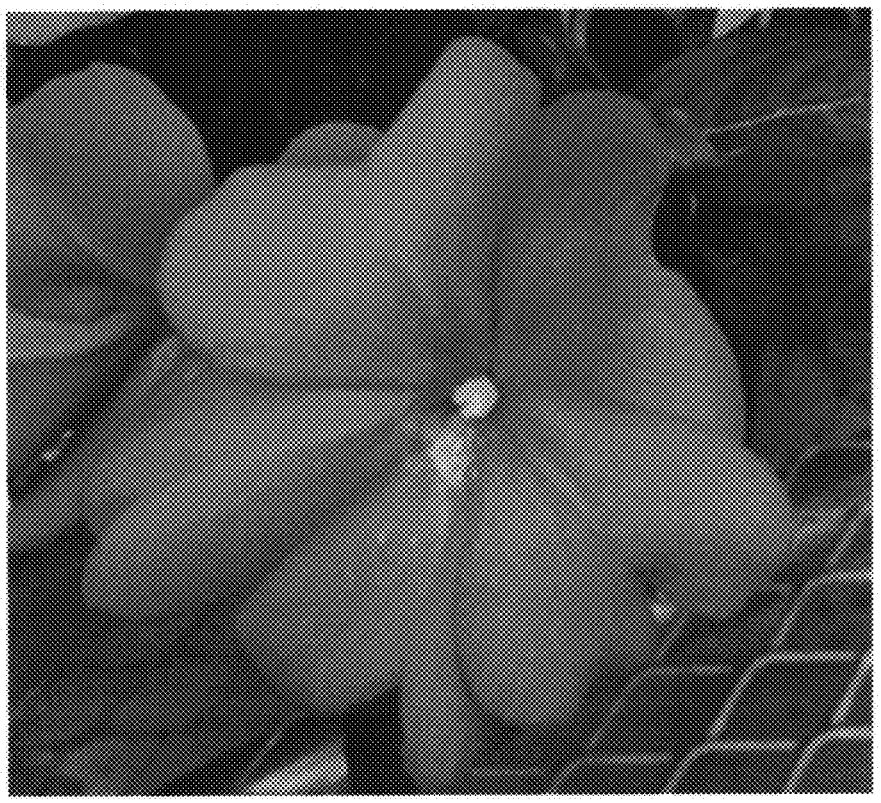
Figure 2:
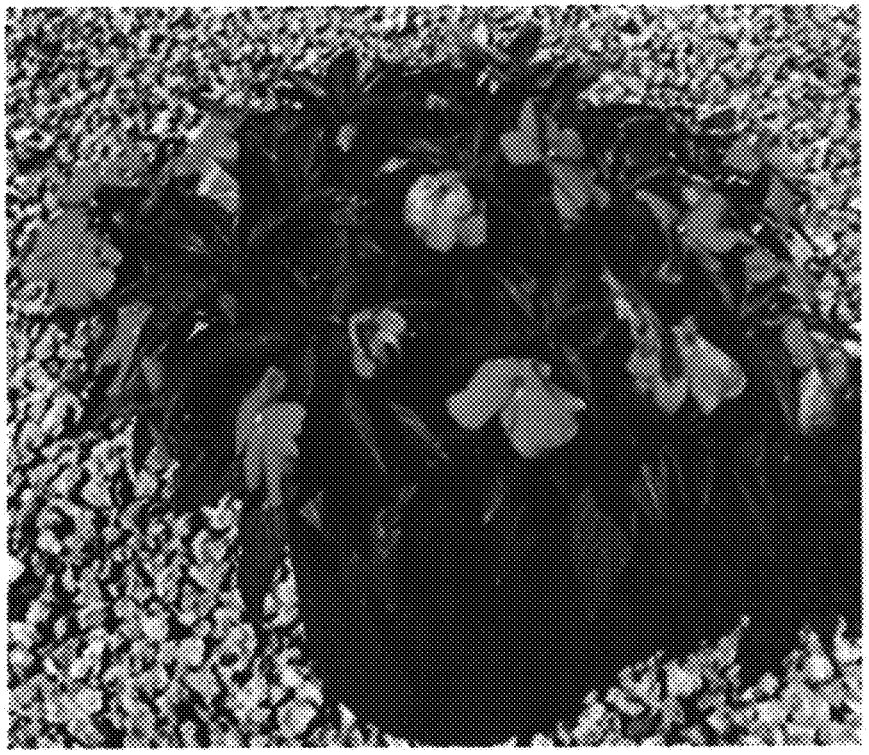

The photographic drawings show in FIG. 1 a close-up of the flowers and in FIG. 2 a flowering plant of the new variety growing in 14 cm pot.

DETAILED BOTANICAL DESCRIPTION

The aforementioned photographs were taken in March 2021 from plants grown in a greenhouse trial in Gilroy, Calif. USA. These plants were growing in 10 cm pots and were approximately 16 weeks of age.

The plant descriptions and measurements were taken in May 2021, on 16-week old plants growing in a greenhouse in Gilroy, Calif. USA. Cuttings were stuck in week 2 for rooting, planted into 10 cm pots in week 6, and were grown, without pinching, on benches in a greenhouse, initially at a day temperature of 18° C. and night temperature of 16° C. However, day temperatures often raised above 20° C.

Color references are made to The Royal Horticultural Society Colour Chart (R.H.S.) 2001.

TABLE 1

DIFFERENCES BETWEEN THE NEW VARIETY 'IMGZ0020' AND SIMILAR PATENTED VARIETIES

| | 'IMGZ0020' | 'NG061' ('Sonic Pink') (Not patented) | 'NG087' ('Super Sonic Pink') (Not patented) |
|---|---|---|---|
| Flower color: | Pink | Pink | Pink |
| Flower pattern: | Solid | Not solid | Not solid |
| Habit: | Medium | Medium | Medium |
| Branching: | Better | Less | Less |

Plant:

*Form, growth and habit.*—Medium sized, mounded, well branched.

*Plant height.*—21.5 cm (without pot), 32 cm (with pot).

*Plant height (inflorescence included).*—23.0-24.0 cm (without pot).

*Plant width.*—39.0 cm.

Roots:

*Number of days to initiate roots.*—6 days at about 22 degrees C.

*Number of days to produce a rooted cutting.*—14-16 days at 22 degrees C.

*Type.*—Fibrous, free branching.

*Color.*—RHS 159A.

Foliage:

*Arrangement.*—Simple leaves, mainly in whorls.

*Young leaf, color upper surface.*—RHS 141A.

*Young leaf, color lower surface.*—Closest RHS 137A.

*Mature leaf, color upper surface.*—RHS 136A.

*Mature leaf, color lower surface.*—Closest to RHS 133A.

*Length.*—Up to 9-9.7 cm.

*Width.*—Up to 2.8-3.2 cm.

*Shape.*—Lanceolate.

*Base shape.*—Lanceolate.

*Apex shape.*—Acuminate.

*Margin.*—Serrulate, with short bristles.

*Texture.*—Slightly waxy and glossy on the upper surface, glabrous on both surfaces.

*Color of veins, upper surface.*—RHS 137D.

*Color of veins, lower surface.*—RHS 47A.

*Petiole color, upper side.*—RHS 39B.

*Petiole color, lower side.*—RHS 53B.

*Length.*—Up to 2 cm.

*Diameter.*—0.3 cm.

*Texture.*—Glabrous.

Stem:

*Color of stem.*—RHS 184A.

*Length of stem.*—About 14 cm.

*Diameter.*—1.3-1.5 cm.

*Length of internodes.*—Approximately 2.0 to 4.0 cm.

*Texture.*—Smooth, glabrous.

*Number of branches.*—8 main branches plus 20 side branches per main branch.

*Color of peduncle.*—RHS 45B.

*Length of peduncle.*—5.0-5.2 cm.

*Peduncle diameter.*—0.2-0.3 cm.

*Texture.*—Glabrous.

Inflorescence:

*Blooming habit.*—Continuous flowering from late spring through fall.

*Type of inflorescence.*—Solitary flowers emerge from the upper leaf nodes of the stem.

*Number of flowers per node.*—2-4 open flowers and additional buds in various stages of development.

*Quantity of flowers per plant.*—20 open flowers plus 25 (big and small) buds (10 cm pot plant in October).

*Lastingness of individual blooms on the plant.*—About 8-10 days.

*Fragrance.*—None.

Bud (just before opening):

*Color.*—RHS 67C.

*Length.*—Up to 2.4 cm.

*Width.*—Up to 1.7 cm.

*Shape.*—Ovate.

Immature flowers:

*Color of petals, upper surface.*—RHS 67B.

*Color of petals, lower surface.*—RHS N74B.

Mature flowers:

*Flower, vertical length.*—8.5 cm.

*Flower, horizontal width.*—9.0 cm.

*Flower depth.*—0.8-1.2 cm.

*Color of petals, upper surface.*—RHS 68A.

*Color of petals, lower surface.*—RHS N74D.

*Petal shape.*—Heart shaped.

*Petal apex shape.*—Broadly obcordate.

*Petal margin.*—Entire.

*Petal texture, upper surface.*—Papillose.

*Petal texture, lower surface.*—Papillose.

Calyx:

*Arrangement.*—One large sepal bearing the spur, 2 small, lateral sepals, and 1 fused keel.

*Large sepal(s).*—

*Color, visible surface.*—RHS 65A.

*Length.*—2.0 cm.

*Width.*—1.3 cm.

*Shape.*—Ovate.

*Apex shape.*—Aristate.

*Base.*—Fused with the spur.

*Margins.*—Entire.

*Texture, upper surface.*—Papillose.

*Texture, lower surface.*—Papillose.

*Lateral sepals.*—

*Color of surface.*—RHS 48A.

*Length.*—1.5 cm.

*Width.*—0.7-0.8 cm.

*Shape.*—Ovate.

*Apex shape.*—Acuminate.

*Base.*—Fused.

*Margins.*—Entire.

*Texture, upper surface.*—Glabrous.

*Texture, lower surface.*—Glabrous.

*Keel color.*—From RHS 46A.

Spur:

*Color.*—RHS 61B.

*Length.*—5.6-5.8 cm.

*Diameter.*—0.3 cm at the base, 0.1 cm at tip.

Reproductive organs:

Androecium: 5 stamen, fused with the anthers hooded.

*Diameter of androeceum.*—0.6 cm.

*Surface color.*—RHS 32D, fading towards margin.

*Pollen amount.*—Few.

*Color of pollen.*—RHS 8D.

Gynoecium:

*Pistil*.—One, elongate.

*Pistil length*.—0.5-0.6 cm.

*Stigma color*.—RHS 76D.

*Ovary color*.—RHS 144A.

*Fertility/seed set*.—Has not been observed on this hybrid.

*Disease/pest resistance*.—Has not been observed on this hybrid. However, it is known for *Impatiens interspecific* that it is downy mildew resistant.

What is claimed is:

1. A new and distinct variety of *Impatiens interspecific* plant named 'IMGZ0020' substantially as illustrated and described herein.

* * * * *